United States Patent [19]

Schroeder

[11] 4,088,893

[45] May 9, 1978

[54] HEAD ORIENTING DEVICE FOR CEPHALOMETRIC X-RAYS

[76] Inventor: Charles H. Schroeder, P.O. Box 9414, Raytown, Mo. 64133

[21] Appl. No.: 765,985

[22] Filed: Feb. 7, 1977

[51] Int. Cl.² ............................................. G21K 5/08
[52] U.S. Cl. .................................... 250/451; 250/456; 250/491
[58] Field of Search ......................... 250/451, 456, 491

[56] References Cited

U.S. PATENT DOCUMENTS

| 2,264,410 | 12/1941 | Schier | 250/451 X |
| 2,532,967 | 12/1950 | Thompson | 250/451 X |

Primary Examiner—Archie R. Borchelt
Attorney, Agent, or Firm—Lowe, Kokjer, Kircher, Wharton & Bowman

[57] ABSTRACT

A wire device is pivotally attached to one ear post of a head positioning mechanism of the type used in cephalometric radiography. The wire may be pivoted to an indicating position wherein one of its ends indicates the proper location of the orbital area for correct head orientation. The wire provides a straight line on the X-ray film which represents an indication of the Frankfort plane. The wire may also be pivoted to an out of the way retracted position.

9 Claims, 3 Drawing Figures

U.S. Patent
May 9, 1978
4,088,893
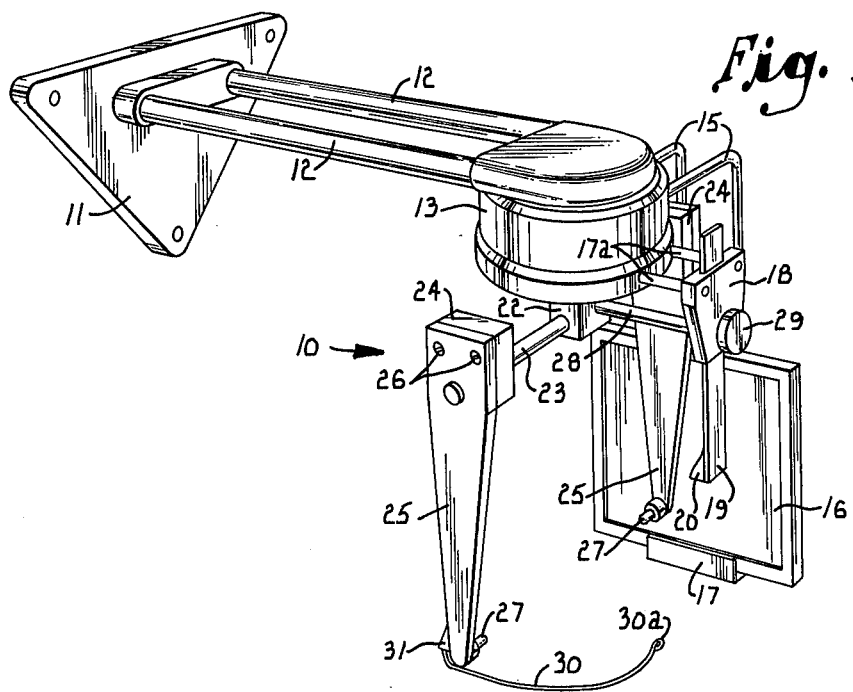
Fig. 1.
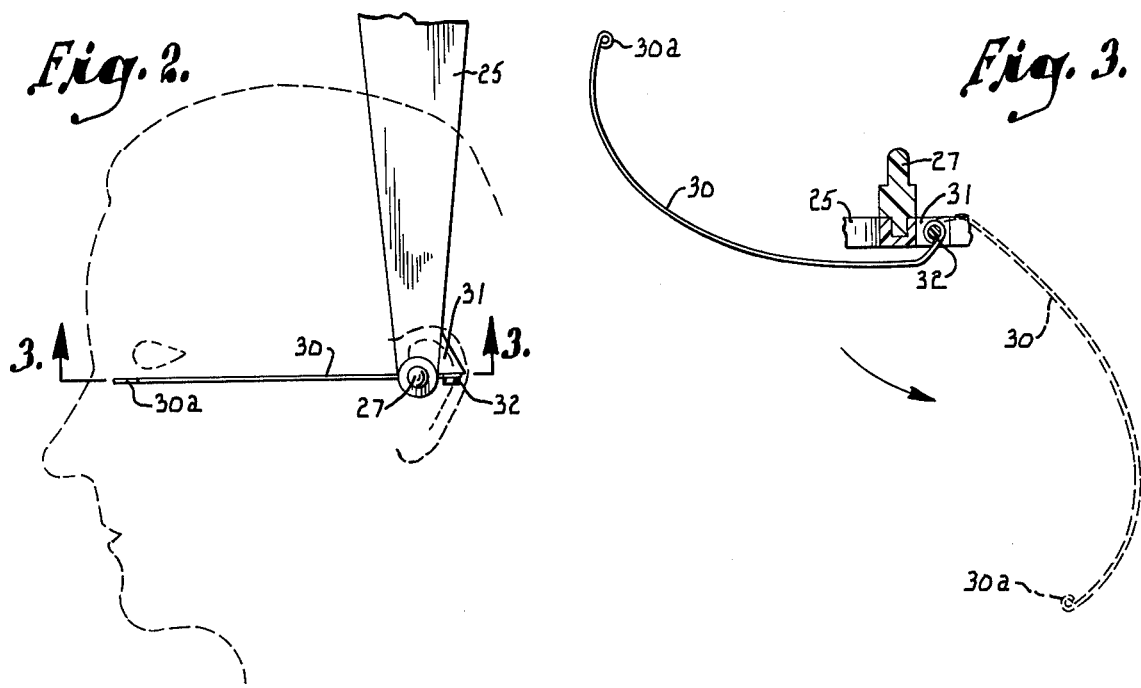
Fig. 2.
Fig. 3.

HEAD ORIENTING DEVICE FOR CEPHALOMETRIC X-RAYS

BACKGROUND AND SUMMARY OF THE INVENTION

This invention relates to a device that may be attached to a head positioning unit to indicate the orientation at which the head should be maintained for effective cephalometric radiography.

In the field of orthodontics, analysis of the skeletal and tooth structure is made from X-ray photographs that are taken laterally of the face. For each set of X-rays, the head must be positioned and oriented identically in order to provide a basis upon which to determine the type of treatment necessary or the improvement that is being made during the course of treatment. Accurate comparison between the different sets of X-ray photographs can then be made and any changes in the skeletal structure can be readily ascertained. The cephalometer mechanisms which are used to position the head typically include a pair of vertical ear posts which contact opposite sides of the head to locate it properly between the X-ray machine and the cassette which contains the X-ray sensitive film.

It is also necessary to provide a means for repeatably orienting the head at the proper tilt angle with respect to horizontal. Ordinarily, the porion or ear canal and the infra-orbital notch area at the bottom of the orbital canal should be in the same horizontal plane, which is commonly known as the Frankfort plane. The ear posts usually have small rods or pins which fit into the ears, and a pointer device is provided to indicate the proper position of the orbital area for correct orientation of the head. The pointer is carried on a support arm which attaches to the main superstructure of the head holder in a manner to fold or telescope down such that the pointer is at the same elevation as the ear pins. When the head is oriented with the orbital area at the same elevation as the pointer, proper tilting of the head is established.

Even though this conventional pointer assembly has been widely used, it has not been entirely satisfactory in many respects. If the pointer remains in its down or indicating position to assure that the head remains in the proper orientation during the X-ray process, it shows up in the X-ray photograph at a location where it can obscure important areas of the skeletal structure. Moreover, the pointer is mounted to the main superstructure of the head holder, and it therefore requires a complicated mounting assembly which allows it to be folded or telescoped up and down. Manifestly, this adds substantially to the complexity and expense of the device, while increasing the time and difficulty involved in properly positioning the head.

In view of these deficiencies in the conventional pointer mechanism, it is the primary goal of the present invention to provide an improved device for indicating the orientation at which the head should be maintained during the cephalometric X-ray process.

More specifically, it is an object of the invention to provide a device of the character described which is adapted to be attached directly to the ear posts of existing head positioning mechanisms in order to avoid the expense and complexity of an additional mounting assembly.

Another object of the invention is to provide a device of the character described which may be pivotally attached to the ear post in order to be quickly and easily moved into and out of indicating position.

Still another object of the invention is to provide a device of the character described which may be attached to a wide variety of existing head positioning mechanisms.

A further object of the invention is to provide a device of the character described which provides a permanent mark of the Frankfort plane on the X-ray film and which does not obscure any important areas of the film. Since the indicating device comprises a small diameter wire which is located entirely in the horizontal Frankfort plane, it may be left in place to provide a single straight line which indicates the Frankfort plane on the X-ray film. Alternatively, the wire may be pivoted to a retracted position near the rear of the skull where the bone structure is not important from an orthodontic standpoint.

An additional object of the invention is to provide a device of the character described which is simple and economical to construct and safe and accurate in use.

Other and further objects of the invention, together with the features of novelty appurtenant thereto, will appear in the course of the following description.

DETAILED DESCRIPTION OF THE INVENTION

In the accompanying drawing which forms a part of the specification and is to be read in conjunction therewith and in which like reference numerals are used to indicate like parts in the various views:

FIG. 1 is a perspective view showing a device constructed according to the present invention attached to a conventional head positioning unit of the type used in cephalometric radiography;

FIG. 2 is a fragmentary elevational view illustrating the manner in which the device is used to properly orient a human head which is shown in broken lines; and FIG. 3 is a fragmentary plan view taken partially in section along line 3—3 of FIG. 2 in the direction of the arrows, with the broken lines indicating movement of the device to its retracted position.

Referring now to the drawing in more detail and initially in FIG. 1, reference numeral 10 generally designates a conventional head positioning unit of the type commonly used in orthodontic radiography. A mounting plate 11 provides a means for attaching the unit to a wall or similar supporting surface. A pair of parallel arms 12 extend horizontally from plate 11 and carry a main support cylinder 13 on their outer ends. The cylinder 13 is preferably mounted in a manner to rotate about a vertical axis.

A pair of bent rods 15 extend from the rear side of cylinder 13 to provide support for a rectangular cassette 16 which contains X-ray sensitive film. Rods 15 are bent to extend vertically throughout most of their length, and a cassette holder 17 is mounted on their lower ends to support the cassette 16 in position to receive the incoming X-ray beam which is directed from a conventional X-ray machine (not shown). A pair of short rods 17a extend horizontally from the side of cylinder 13 and carry a plate bracket 18 which supports a vertical post 19. The lower end of post 19 carries a nasion rest 20 against which the bridge of the nose may be positioned. Post 19 is vertically adjustable in order to vary the elevation of the nasion rest 20.

A block 22 which depends from the underside of cylinder 13 receives a pair of horizontal arms, one of which is designated by numeral 23. The arms 23 extend in opposite directions from block 22, and each arm carries a mounting block 24 on its outer end. An ear post 25 is attached to each block 24 by screws 26. Each ear post 25 extends vertically below its mounting block 24, and each ear post is provided with a small, inwardly projecting ear plug or pin 27 on its lower end.

Arms 23 are supported in a manner to extend and retract axially with respect to block 22, so that the ear posts 25 may be moved toward and away from one another. A conventional rack and pinion mechanism (not shown) located within block 22 connects arms 23 with one another in a manner to extend or retract each post 25 an equal distance but an opposite direction, thereby assuring that the head will be maintained in a centered position with respect to the unit. A rotatable shaft 28 which carries the pinion (not shown) may be rotated to effect movement of the ear posts 25 inwardly and outwardly. Shaft 28 extends through bracket 18 and is provided with a handle 29 to facilitate its rotation.

As thus far described, the head positioning unit is constructed conventionally, and its purpose is to locate the head properly between the X-ray machine (not shown) and the cassette 16.

In accordance with the present invention, a curved wire 30 is provided to assist in orienting the head properly with respect to horizontal. The wire 30 is pivotally attached to the ear post 25 which is farther from the cassette 16. As best shown in FIG. 2, a triangular mounting block 31 is seucred to the rear edge of post 25 by glue or in any other suitable manner. Extending below block 31 is a vertical stud 32 having an enlarged head which is spaced a short distance below the flat bottom surface of the block. One end of wire 30 is looped around the shank of stud 32 such that it is held tightly but pivotally between the stud head and the lower surface of block 31. The wire is able to pivot about its end on the vertical pivot axis of stud 32 between the indicating position shown in solid lines in FIG. 3 and the retracted position shown in broken lines. Wire 30 is at the same elevation as the adjacent ear pin 27, as best illustrated in FIG. 2.

Preferably, wire 30 is a rather stiff spring wire having a diameter of approximately 0.03 inch. The wire is gradually curved so that it is able to curve around the side of the head and facial area when in the indicating position, and its outer end 30a is rounded or looped to avoid presenting a sharp tip. As shown in FIG. 2, the entirety of wire 30 is contained in a single horizontal plane which also passes through the ear pin 27.

In use, the head is positioned between ear posts 25 with wire 30 in the retracted position, and handle 29 is turned until the ear posts engage opposite sides of the head with the pins 27 received in the ears. This locates the head properly with respect to the X-ray machine (not shown) and the cassette 16. To orient the head at the proper tilt angle with respect to horizontal, wire 30 is pivoted to its indicating position which is the position shown in solid lines in FIG. 3. The head is then tilted until the looped wire end 30a is located near or against the face immediately below the eye at the area of the infra-orbital notch. This position of the head is shown in FIG. 2, and it is pointed out that the ear canal and the infra-orbital notch are located in the same horizontal plane which also contains wire 30.

The X-ray process may then proceed, preferably with wire 30 remaining in the indicating position to assure that the head is maintained in the proper orientation. The metal wire will show up on the X-ray film as a straight horizontal line extending between the porion of ear canal and the infra-orbital notch. Normally, this line must be subsequently drawn in on the film since it represents the horizontal plane known as the Frankfort plane which provides a basis for analysis of the skeletal structure. However, since the wire 30 of the present invention provides an accurate mark indicating the Frankfort plane, the necessity of subsequently marking this line on the film is avoided.

If it is not desired to provide a mark of the Frankfort plane on the X-ray film, wire 30 may be pivoted to the retracted position shown in broken lines in FIG. 3. In this position, the wire is located at the rear of the skull where it will not obscure any of the skeletal structure which is important to the cephalometric analysis of the X-ray photograph.

It is noted that the wire 30 may be readily attached to head positioning mechanisms other than the unit 10 which is shown in the drawing. It is further noted that wire 30 is attached directly to the ear post, and the necessity of providing a separate mounting assembly is thus avoided.

From the foregoing, it will be seen that this invention is one well adapted to attain all the ends and objects hereinabove together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:

1. An attachment for a head positioning device which includes at least one substantially vertical post member having an ear contacting portion for engagement with the ear, said attachment comprising:

an indicating member having an end portion for assisting in the orientation of the head with respect to horizontal; and means for mounting said indicating member on said post member for pivotal movement about a substantially vertical pivot axis between an indicating position wherein said end portion is located in proximity to the facial area at substantially the same elevation as said ear contacting portion, and a retracted position wherein said end portion is remote from the facial area.

2. The invention set forth in claim 1, wherein substantially the entirety of said indicating member is located in a single plane, and said mounting means is adapted to locate said indicating member in a substantially horizontal plane which contains said ear contacting portion.

3. The invention set forth in claim 2, wherein said indicating member comprises a thin metal wire element of curved configuration.

4. The invention set forth in claim 1, wherein said mounting means comprises:

a mounting member adapted to be attached to said post member in proximity to said ear contacting portion; and means connecting said indicating member with said mounting member at substantially the elevation of said ear contacting portion and for pivotal movement about said vertical pivot axis between said indicating and retracted positions.

5. The combination set forth in claim 1, wherein said mounting means locates said indicating member between a source of X-rays and the facial area.

6. In a head positioning device for use in cephalometric radiography, the combination of:
 a pair of spaced apart post members supported on the device and adapted to engage opposite sides of the head;
 an ear pin on at least one post member for engagement with the ear;
 an indicating member having first and second end portions; and
 means mounting said indicating member on said one post member for pivotal movement about a substantially vertical pivot axis between an indicating position wherein said first end portion is adapted to contact the facial area of a head positioned between the post members, and a retracted position wherein said first end portion is remote from the facial area.

7. The combination set forth in claim 6, wherein said indicating member comprises a thin metal wire element extending in a curved fashion between said first and second end portions and located substantially entirely in a generally horizontal plane which is substantially coextensive with a horizontal plane passing through said ear pin.

8. The combination set forth in claim 7, wherein said mounting means connects said wire element with said one post member for movement about a substantially vertical pivot axis located at said second end portion.

9. The combination set forth in claim 6, wherein said mounting means locates said indicating member between a source of X-rays and the facial area.

* * * * *